(12) United States Patent
Crouch

(10) Patent No.: US 11,452,785 B1
(45) Date of Patent: Sep. 27, 2022

(54) VIRAL RADIOPHARMACEUTICALS FOR THE TREATMENT/CURE OF COVID-19 AND OTHER VIRUSES

(71) Applicant: Zachary Charles Crouch, Knoxville, TN (US)

(72) Inventor: Zachary Charles Crouch, Knoxville, TN (US)

(73) Assignee: Zachiry Charles Crouch, Knoxville, TN (US)

( * ) Notice: Subject to any disclaimer, the term of this patent is extended or adjusted under 35 U.S.C. 154(b) by 0 days.

(21) Appl. No.: 16/894,179

(22) Filed: Jun. 5, 2020

(51) Int. Cl.
*A61K 51/00* (2006.01)
*A61M 36/14* (2006.01)
*A61K 51/04* (2006.01)

(52) U.S. Cl.
CPC .................................. *A61K 51/04* (2013.01)

(58) Field of Classification Search
CPC ....................................................... A61K 51/04
USPC ......................................................... 424/1.65
See application file for complete search history.

(56) References Cited

FOREIGN PATENT DOCUMENTS

CN 110305036 A * 10/2019

OTHER PUBLICATIONS

Meng et al. Chem. Sci. 2019, 10, 7156-7162. (Year: 2019).*
Chamberland University of Maine, 1966, 1-18. (Year: 1966).*
Wade et al. Nature 1967, 1303-1304. (Year: 1967).*

* cited by examiner

*Primary Examiner* — Michael G. Hartley
*Assistant Examiner* — Sean R Donohue

(57) ABSTRACT

In general, the patent herein is a radioactive chemical which attaches to the virus and releases radiation which kills the virus. Specifically, the chemical is an alpha-ketoamide designed to attach to the virus. However, instead of 2 bromine atoms, Iodine-131 is at the location of where the bromine atoms would have been. Iodine-131 is a radioactive element which releases ionizing radiation. The virus with which this radioactive chemical is designed for is the COVID-19 coronavirus, although the patent is for any virus. Since, modifications can be made in chemical structure and radioactive chemical species, the patent is for any and all chemicals which contain any type of radioactive element to kill or disrupt any type of virus.

1 Claim, 1 Drawing Sheet

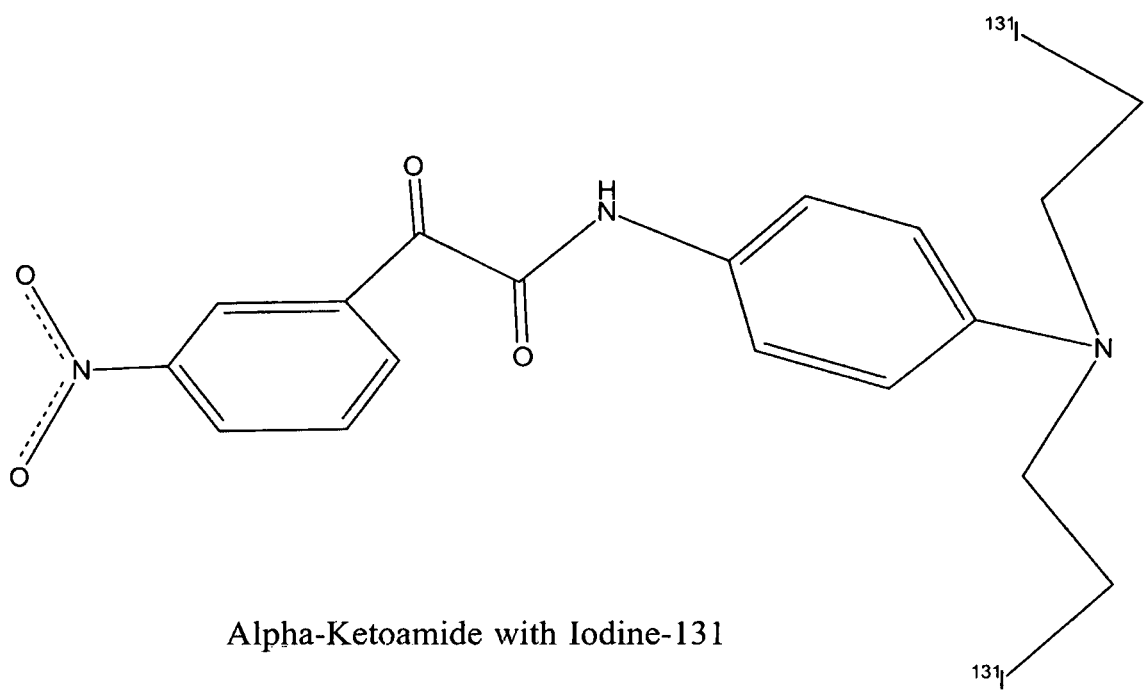
Alpha-Ketoamide with Iodine-131
FIG. [1]
$[C_{18}H_{17}O_4N_3(I\text{-}131)_2]$
FIG. [2]

VIRAL RADIOPHARMACEUTICALS FOR THE TREATMENT/CURE OF COVID-19 AND OTHER VIRUSES

Technical Field: In general, the patent herein is a radioactive chemical which attaches to the virus and releases radiation which kills the virus. Specifically, the chemical is an alpha-ketoamide designed to attach to the virus. However, instead of 2 bromine atoms, Iodine-131 is at the location of where the bromine atoms would have been. Iodine-131 is a radioactive element which releases ionizing radiation. The virus with which this radioactive chemical is designed for is the COVID-19 coronavirus, although the patent is for any virus. Since, modifications can be made in chemical structure and radioactive chemical species, the patent is for any and all chemicals which contain any type of radioactive element to kill or disrupt any type of virus.

Background Art: The claim of the alpha-ketoamide chemical with Iodine-131 is that this organic molecule attaches to a virus and the radiation released from Iodine-131 kills the virus. The virus is the coronavirus, COVID-19, although will work with other viruses as well. The organic molecules serve the purpose of attaching to the virus so that the radioactive element is close to the virus. The radioactive element serves the purpose of sending radiation to the virus. This radiation contains energy which break bonds of the virus, killing it.

Disclosure of Invention: The scope of this claim applies to all viruses. The scope of this claim applies to any chemical with any radioactive elements. The scope of this claim applies to any type of radioactive element.

Industrial Applicability: This radioactive chemical can be taken as a pill or injected into the blood to treat or cure viruses including COVID-19.

BRIEF DESCRIPTION OF THE DRAWINGS

FIG. [1]: Chemical Structure of Alpha-Ketoamide with Iodine-131

FIG. [2]: Chemical Formula for Alpha-Ketoamide with Iodine-131

The invention claimed is:

1. A method of treating COVID-19 comprising administering the compound

* * * * *